United States Patent

Rhenter et al.

[11] Patent Number: 5,078,745
[45] Date of Patent: Jan. 7, 1992

[54] SYNTHETIC LIGAMENT FOR THE KNEE

[76] Inventors: Jean-Luc Rhenter, 11 rue de l'Annonciade, 69001 Lyon; Jean Collomb, L'Olangnier, 26800 Portes les Valence, both of France

[21] Appl. No.: 415,245
[22] PCT Filed: Dec. 22, 1988
[86] PCT No.: PCT/FR88/00634
  § 371 Date: Aug. 16, 1988
  § 102(e) Date: Aug. 16, 1988
[87] PCT Pub. No.: WO89/05614
  PCT Pub. Date: Jun. 29, 1989
[51] Int. Cl.⁵ ............................................. A61F 2/08
[52] U.S. Cl. ........................................................ 623/13
[58] Field of Search ...................... 623/13, 11, 16, 18

[56] References Cited

U.S. PATENT DOCUMENTS 4,411,027 10/1983 Alexander et al. .................... 623/18
4,863,471 9/1989 Mansat .................................. 623/13

FOREIGN PATENT DOCUMENTS 0236821 9/1987 European Pat. Off. .
0239775 10/1987 European Pat. Off. .
0249346 12/1987 European Pat. Off. .
2135825 12/1972 France .
2213761 8/1974 France .
2596641 10/1987 France .
2598311 11/1987 France .
2598315 11/1987 France .

Primary Examiner—David J. Isabella
Attorney, Agent, or Firm—Parkhurst, Wendel & Rossi

[57] ABSTRACT

A synthetic ligament for knees, made of biocompatible material, including an active ligamentary part arranged between the femoral and tibial regions of intra-articular penetration. The active ligamentary part having a first pair of parallel main elements and a second pair of intermediate elements which are crossed and integral with the first pair of main elements at the region of intra-articular penetration of the knee joint.

6 Claims, 4 Drawing Sheets

SYNTHETIC LIGAMENT FOR THE KNEE

The present invention relates to a new type of synthetic ligament particularly designed for replacing the anterior cruciate ligament of the knee.

The anterior cruciate ligament of the knee joins the intercondylar area of the tibia to the intercondylar fossa of the femur. Its principal role is to check the forward slipping of the tibia, that is to say, to reduce the anterior drawer movements.

Orthopedic surgery of the knee has progressed greatly in recent years and there is an increasing tendency to offer ligament replacement prostheses.

Replacement prostheses for the anterior cruciate ligament in the knee proposed heretofore consist of a single bundle of synthetic fibers or groups of synthetic fibers which all terminate at one and the same site at each of the ends of the bundle. This prosthesis makes it possible to replace the anterior cruciate ligament and to limit the anterior displacement of the tibia under the femur created by the connection of the ligament to be replaced.

However, this system with a single bundle of fibers or groups of fibers limits this drawer movement only at certain degrees of flexion. In effect, a single bundle of fibers does not provide isometric tension of the synthetic ligament at every degree of flexion, i.e., tension without shortening the ligament. Such a ligament is described in one of the embodiments of a surgical instrument designed for placement on the joints of such ligaments in French Patent Application A 2 2598 311. This ligament is single-stranded and, when placed in the joint, goes through a simple back-and-forth movement from the anterointerior surface of the tibia around a point of anchorage in the femur. In this way, as a result of the independence of the forward-moving strand in relation to the return strand, stresses are never transmitted from one strand to the other, which reduces the resistance of the strand under stress and hence its useful life. In addition, this ligament, such as described, in no way prevents the anterior drawer movements of the tibia under the femur.

In point of fact, the inability of a single-stranded ligament to limit the anterior drawer movements of the tibia under the femur is inherent in the variation of the radii of curvature of the femoral condyles at the lower end of the femur, the condyles being in contact with the tibia in the glenoid cavity. These radii vary from front to back, also producing a front-to-back displacement of the instant flexion-rotation centers of the knee during flexion. Put differently, because of the presence of the femoral condyles with variable curvature radii and also because of the nonphysiological elasticity of these synthetic ligaments, continuous isometric tension of such a single-stranded ligament cannot be achieved.

It was then proposed to resort to two single-stranded ligaments to overcome this overwhelming drawback. U.S. Pat. No. 4,411,027 describes a patellar suture material made from two individual strands. Actually, it uses not one, but two, suture materials. These two materials are placed ahead of the knee joint by the classic "bracing" technique, which means that one of the suture materials simply goes around two points of support placed, respectively, on the quadriceps tendon (at the lower end of the anterior muscle of the thigh also known as the quadriceps) and on the tibia, and describes an oval, and the other one, also attached through the two points of support mentioned above, describes an 8. To this day, this technique is well known in connection with patellar tendon repair. However, it has some considerable disadvantages. First of all, the fact that several suture materials are used means that, when the joint is working, one of the strands slides in relation to the other, and as a result produces friction. This is certainly favorable for the healing of the patellar tendon, but causes premature and redhibitory wear of the strands as they pass through the tendon and the tibia, and in no way permits them to act as a prosthetic device. Next, as in the previous case, because the two strands are independent, the stresses are never transmitted from one strand to the other, which then reduces the resistance of the strand under stress and thus affects its useful life. In addition, in order to make it possible to attach the two strands to the joint, it is necessary to hollow out relatively large tunnels in the bone and tendon concerned to permit the passage of the two strands, thus weakening the former. Finally, if it is desired to apply the teachings of this document to the replacement of the anterior cruciate ligament of the knee, the fact that the two strands are not integral and the sliding in the insertion tunnels would mean that, when the joint is working, permanent tension of the prosthesis could not be achieved at every degree of flexion-rotation. In fact, it should be noted that this document does not claim a ligament prosthesis, but rather an absorbable suture material in connection with patellar tendon repair, so that the application and purpose are different.

The object of the present invention is to overcome these disadvantages. It proposes a prosthesis for a synthetic ligament for the knee joint made of biocompatible material comprising an active part of the ligament placed between the femoral and tibial intra-articular penetration areas, defining the entrances of tunnels made in the femur and in the tibia, respectively, and from the exit of which emerge the ends of the ligament, the ends forming ties to be attached to the femur and the tibia, respectively.

It is characterized in that the active part of the ligament comprises:

a first set of two principal elements that are substantially parallel, extended by the ties, integral with each other at the level of the active part of the ligament, as well as a second set of two intermediate elements that are crossed at the level of the active part of the ligament and integral with the first set of principal elements starting from, and at the level of, the femoral and tibial intra-articular peneration areas, in the direction of the exit of the tunnels.

In other words, the present invention relates to a prosthesis for a synthetic cruciate ligament of the knee, consisting of two independent bundles of synthetic fibers or groups of fibers, each ending in an upper condyle and lower glenoid (tibial) end, independent from each other, integral with two groups of fibers of the same kind, connecting the independent bundles with each other. Put differently, the ligament proposed in the present invention is he multistrand type, but constitutes only a single entity.

Advantageously, in practice:

the femoral insertion areas of the principal elements are different;

the ligament is made of a one-piece textile material;

the first and second sets second sets of elements are made of a biocompatible knit textile material, and the second set of intermediate element emerges from the first set of principal elements in the vicinity of the femoral and tibial intra-articular penetration areas;

the interlocking areas of the principal elements at the level of the active part of the ligament are constructed by means selected from among the group consisting of braiding, knitting, welding and sewing;

the biocompatible textile material is a monofilamentous or multifilamentous material selected from the group consisting of polyesters, polypropylene and glass;

the intermediate elements are made integral with the principal elements by welding and, in particular, by heat sealing;

the ends of the ligament forming ties designed to be attached to the tibia and the femur are covered with a polyethylene sheath provided with a needle eye aperture to enable passage of ends in the tunnels.

The manner in which the invention can be implemented and the resulting advantages will be better understood from the consideration of the ensuing embodiment offered solely by way of non-limiting example and from the attached drawings, in which.

Figure 1:
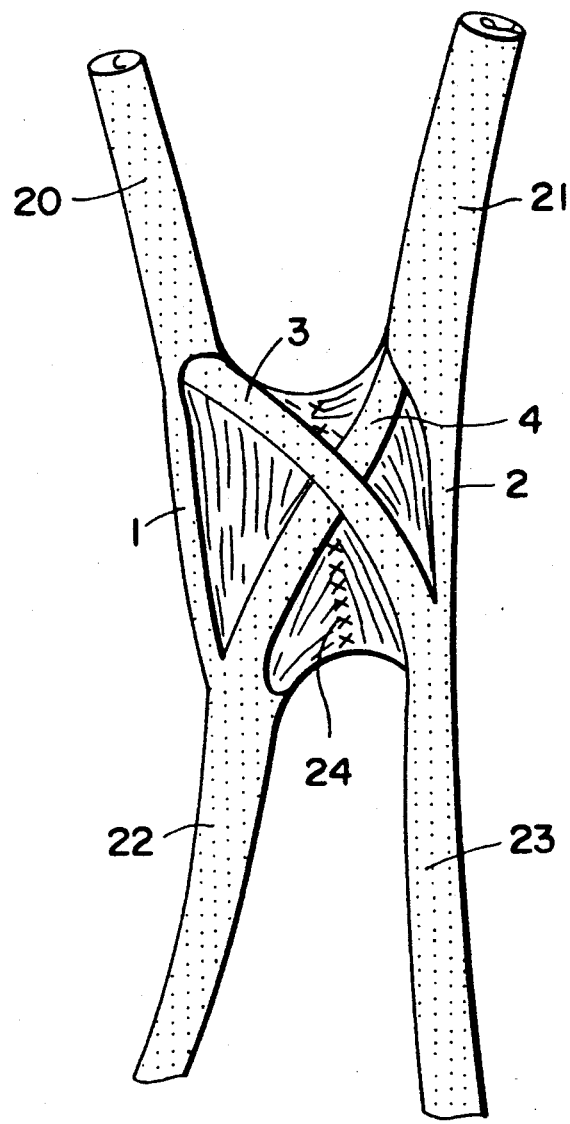
FIG. 1 is a schematic plane representation of a prosthesis according to the invention.

As may be seen in FIG. 1, the anterior cruciate ligament prosthesis according to the invention is in the form of two principal elements (1) and (2), respectively, the posteroexternal bundle (1) and the anterointernal bundle (2).

The length of these two principal elements (1, 2) ranges from 14 to 23 centimeters. They each have a femoral end, (20) and (21) respectively, and a tibial end, (22) and (23) respectively, which act as ties for attaching the ligament to the femur (7) and to the tibia (8), respectively. Their typical diameter is on the order of 5 to 6 centimeters, but it goes without saying that the latter can be adapted to the morphology or activity of the recipient of the prosthesis.

Figure 2:
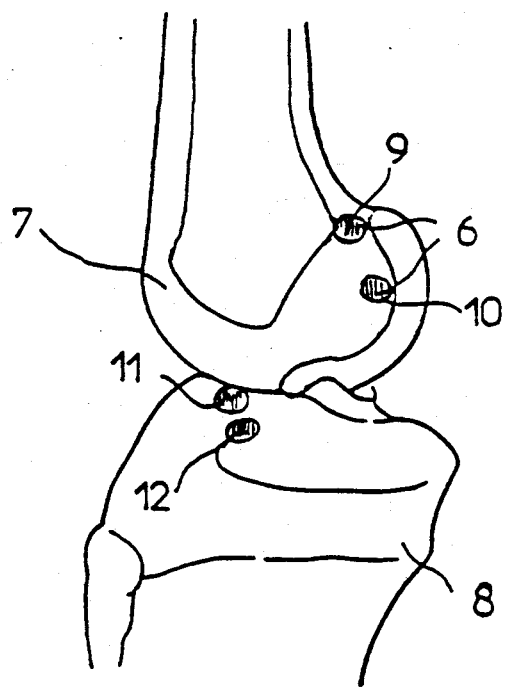
FIG. 2 is a schematic lateral representation of the joint of the right knee from which the internal condyle has been removed, showing the femoral and tibial intra-articular openings for attaching the prostheses, which have been made in the anatomic insertion surfaces of the anterior cruciate ligament.
Figure 5:
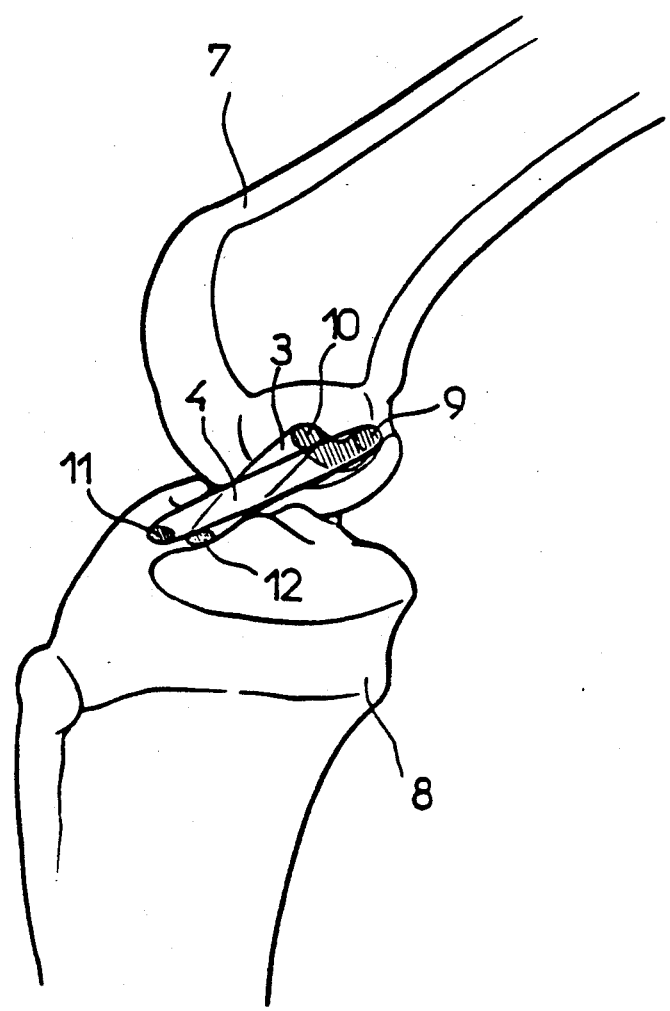
FIG. 5 is a view similar to FIGS. 3 and 4 in which the joint is in an intermediate position in relation to those in FIGS. 3 and 4.

Although they appear parallel in the figure, these two elements are not parallel when fastened in place within the joint. Indeed, as can be seen in FIGS. 2 and 5, when the prosthesis is in place within the joint it is slightly twisted, which is due, on one hand, to the anatomy of the joint and, on the other, to the areas of insertion made therein.

Advantageously, these bundles are in the form of multifilamentous tubular knitwear of biocompatible textile material, in particular polyester.

These elements could, of course, be made in the form of a braid or even monofilamentous tubular knitwear without departing from the spirit of the invention.

Furthermore, in order to protect the bundles and to impart an elastic effect thereto, they are advantageously coated with a layer of biocompatible polyurethane (95) at the level of their field of action in the joint, that is to say, in the active part of the ligament, as well as at the level of the beginning of the ends (20, 21, 22, 23) inserted in the tunnels made in the femur and in the tibia for the purpose of attaching the ties to the femur (7) and to the tibia (8).

These two elements (1) and (2) are inserted at the level of the insertion surfaces of the natural anterior cruciate ligament, except for the fact that the two upper (i.e., femoral) insertions are different. They take place at the level of the posterior internal edge of the external condyle of the femur. The hatched area in FIG. 5 shows the site of the femoral insertion surface of the anatomical ligament.

The lower insertion of the two elements (1) and (2) is also effected at different sites at the level of the anterior prespinal surface of the tibia (8).

According to one important feature of the invention, the two principal elements (1) and (2) are made integral with each other at the level (24) of the active part of the ligament, in particular by knitting. It goes without saying that this could be effected by any other suitable means such as braiding, welding or sewing.

Furthermore, according to another basic feature of the present invention, the ligament also comprises a set of intermediate elements (3, 4), also made of biocompatible textile material. Their typical diameter is from 2 to 3 millimeters.

These elements (3, 4) emerge directly from the principal ligaments (1, 2) at the level of the intra-articular penetration areas (9, 10, 11, 12) and are actually integral with the principal elements (1, 2). These elements (3, 4) are crossed at the level of the active part of the ligament. In other words, the intermediate ligament (3) emerging from the posteroexternal principal element (1) at the level of the femoral intra-articular penetration area (1) goes back into the anterointernal principal element (2) at the level of the tibial intra-articular penetration area (12) Similarly, the intermediate ligament (4) emerging from the anterointernal principal element (2) at the level of the femoral intra-articular area (9) goes back into the posteroexternal principal element (1) at the level of the tibial intra-articular penetration area (11).

The ligament of the invention is actually made of a one-piece textile material. In this way, the intermediate elements are always integral with the principal elements, particularly at the level of, and starting from, the femoral and tibial intra-articular penetration areas in the direction of the exit of the insertion and attachment tunnels of the ligament. Similarly, the principal elements are also integral with each other at the level of the active part of the ligament.

In another embodiment of the present invention, the intermediate elements are also integral with the principal elements at the level of, and starting from, the femoral and tibial intra-articular penetration areas in the direction of the exit of the insertion and attachment tunnels without being an integral part of the principal element, but by welding or heat sealing.

Figure 6:
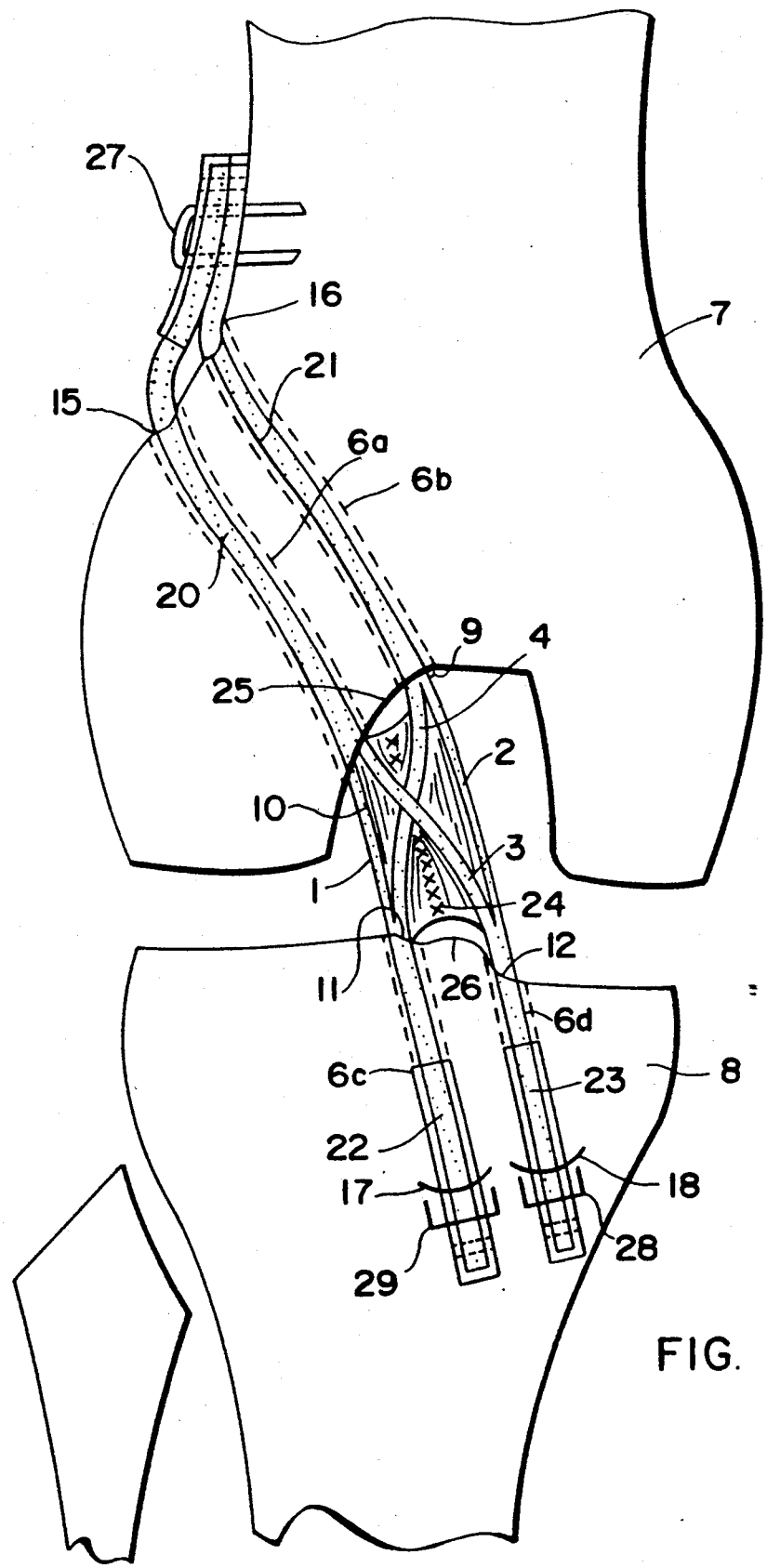
FIG. 6 is a schematic, explanatory view in which the prosthesis is shown in place on the joint, the latter being viewed from the front. This figure is purely schematic and has no other purpose but to facilitate understanding of the invention.

The prosthesis is attached as follows (see FIG. 6): Before anything else and by any suitable means, femoral (6a, 6b) and tibial (6c, 6d) insertion tunnels whose respective femoral (9, 10) and tibial (11, 12) intra-articular openings are shown in FIG. 2, are hollowed out, for example, with drill bits, in the femur (7) and in the tibia (8) at the level of the insertion areas of the natural ligament. The extra-articular femoral and tibial insertion areas of the tunnels are denoted by reference numerals 15, 16 and 17, 18, respectively, in FIG. 6. When making these tunnels, the knee joint is in flexion at about 60-70 degrees. The typical diameter of these tunnels (6) is from 5 to 6 millimeters. The ends of the principal elements (1, 2) are inserted into these tunnels (6) by means of the ties (20, 21, 22, 23) covered by a sheath (not shown) made of polyester and provided with a needle eye aperture to facilitate the insertion. The femoral ends (20, 21) are first pulled upward in order to bring into contact the interlocking area (24) of the two principal elements (1) and (2) with the femoral insertion area (25) situated between the two tunnels (6), they are then twisted together and, finally, are attached to the femur (7) by means of a clip (27) commonly used for this application.

The tibial ties (22, 23) are then attached. First, the interlocking area (24) of the two principal elements (1, 2) is made flush with the area (26) situated between the two tibial intra-articular penetration areas (11, 12). Next, the ties, also covered with a rigid polyethylene sheath with a needle eye aperture, are inserted into the corresponding tunnels (6c, 6d). Then, tension on the order of 10 kilograms is applied to the anterointernal element (2), with the knee joint being in extension, before attaching the element to the tibia by means of a clip (28). Similarly, tension of the same order is applied to the postero-external element (1), with the knee joint being in flexion at an angle of 30 degrees, before attaching it, also by means of a clip (29), to the tibia (8).

Figures 3, 4:
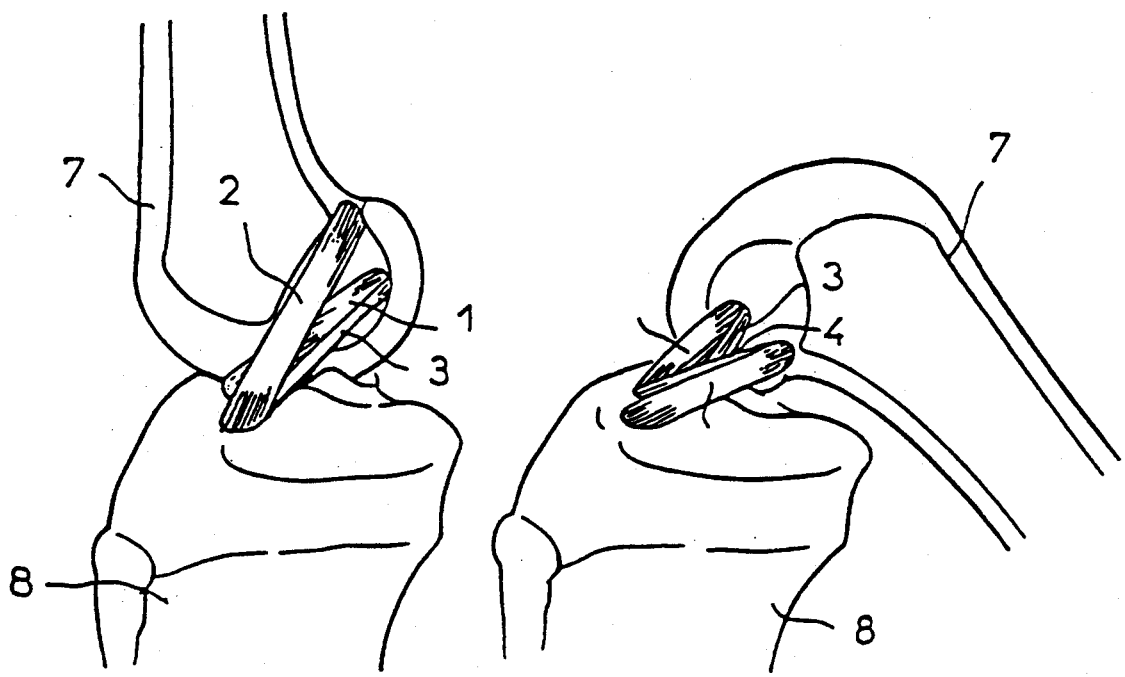
FIG. 3 is a schematic lateral representation of the joint of a right knee in complete extension, the internal condyle of which has been removed and on which the prosthesis according to the invention is in place.
FIG. 4 is a view similar to FIG. 3, but in which the joint is in flexion.

FIGS. 3 to 5 show the ligament according to the invention in place on the joint. In FIG. 3, only the intermediate element (3) can be seen, the other intermediate element (4) being hidden by the anterointernal element (2). In FIG. 4, the two intermediate elements (3, 4) as well as the two principal elements (1, 2) can be seen, with the joint in complete extension. FIG. 5 shows only the intermediate elements (3, 4), so that their positioning within the architecture and the placement of the ligament according to the invention can be shown more clearly.

As indicated in the foregoing description, as a result of the variations in the radii of curvature of the femoral condyles and the way in which the ligament of the invention is placed, one part of the ligament is under tension at all times, thereby limiting or even preventing the anterior drawer movements of the tibia under the femur.

During flexion as shown in FIG. 4, as a result of the variable radii of curvature of the femoral condyles, the tension of the filaments making up the prosthesis thusly constructed is gradually transmitted from the anterior part of the filaments (which are tense during extension) to the posterior part, including the crossing filaments of the intermediate elements. In other words, there is always one part of the filaments making up the elements of the prosthesis which is under tension.

Similarly, during rotation, the two bundles in internal rotation will have a tendency to tighten along their axes, thus reducing the distance between the femoral condyles and the glenoid cavity, causing a coaptation of the articular surfaces.

In external rotation, the two principal elements (1) and (2) will have a tendency to relax and, as a result of their direction, the intermediate elements will limit the tendency toward anterior drawing movements and the tendency toward external rotation.

Thus, at every degree of flexion, this geometrical arrangement makes it possible for a group of fibers to tighten, and the area under tension with this arrangement varies during flexion.

Furthermore, when there are excessive stresses, such as during athletic activities, that is to say, when there is a greater tendency toward anterior drawer movements, a greater quantity of fibers making up the different elements of the ligament of the invention is brought into play to resist and work against these anterior drawer movements. This feature is inherent in the interlocking of different bundles, which increases the mechanical strength of the ligament.

Thus, the present invention offers a number of advantages heretofore not provided by cruciate ligament prostheses, particularly the greater effectiveness of the ligament in controlling the anterior drawer movements and articular coaptation, which absolutely could not be achieved with single-bundle ligaments or with multiligament prostheses.

We claim:

1. A biocompatible synthetic ligament replacement of natural ligaments at the intra-articular area between femoral and tibial bones of a knee joint, including an elongated element terminating at opposite first and second ends, each element comprising:
   first inactive end ties configured to be inserted into first tunnels bored in the femur;
   second inactive end ties configured to be inserted into second tunnels bored in the tibia, wherein said first ties are attached to the femur and extend therefrom to the intra-articular area through said first tunnels, and said second ties are attached to the tibia and extend therefrom to the intra-articular area through said second tunnels; and
   an active midportion intermediate said ends to be positioned in the intra-articular area of the knee joint, comprising:
   (a) first and second substantially parallel principal elements integral at one end to said first ties and at an opposite end to said seconds ties, said principal elements having means for integral connection to each other; and
   (b) a pair of intermediate crossed elements which are freely crossed so as to integrally connect said first principal element to said second principal element, respectively, thereby distributing a load on one of said principal elements at one end thereof to both of said principal elements at the other end thereof.

2. The synthetic ligament of claim 1, wherein said principal elements and said intermediate elements are made of a biocompatible textile material, and wherein said intermediate elements are connected to said principal elements in the vicinity of intra-articular femoral and tibial penetration areas of said tunnels.

3. The synthetic ligament of claim 1, wherein said integral connection of said principal elements has a construction selected from the group consisting of braiding, knitting, welding and sewing.

4. The synthetic ligament of claim 1, wherein said intermediate elements are connected to said principal elements by heat sealing.

5. The synthetic ligament of claim 1, wherein ends of said first ties and said second ties which are attached to the femur and tibia, respectively, include a polyethylene sheath and are provided with a needle eye aperture to enable passage of said ends through said first tunnels and said second tunnels.

6. The synthetic ligament of claim 1, wherein said principal elements and said intermediate elements are made of a one-piece knitted fabric of multifilament yarn selected from the group consisting of polyester, propylene and glass yarns.

* * * * *